United States Patent
Shi et al.

(10) Patent No.: US 10,247,738 B2
(45) Date of Patent: *Apr. 2, 2019

(54) DIAGNOSING AND TREATING ALZHEIMERS DISEASE

(71) Applicant: DIGNITY HEALTH, San Francisco, CA (US)

(72) Inventors: Jiong Shi, Scottsdale, AZ (US); Peng Cheng Han, Charleston, SC (US)

(73) Assignee: DIGNITY HEALTH, San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/962,691

(22) Filed: Apr. 25, 2018

(65) Prior Publication Data

US 2018/0246126 A1 Aug. 30, 2018

Related U.S. Application Data

(63) Continuation of application No. 15/103,059, filed as application No. PCT/US2014/072216 on Dec. 23, 2014, now Pat. No. 9,989,541.

(60) Provisional application No. 61/921,359, filed on Dec. 27, 2013.

(51) Int. Cl.
| | |
|---|---|
| *A61K 38/50* | (2006.01) |
| *G01N 33/68* | (2006.01) |
| *A61K 38/22* | (2006.01) |
| *A61K 38/46* | (2006.01) |

(52) U.S. Cl.
CPC ......... *G01N 33/6896* (2013.01); *A61K 38/22* (2013.01); *A61K 38/46* (2013.01); *A61K 38/50* (2013.01); *C12Y 305/01* (2013.01); *G01N 2333/47* (2013.01); *G01N 2800/2814* (2013.01); *G01N 2800/2821* (2013.01); *G01N 2800/50* (2013.01); *G01N 2800/52* (2013.01)

(58) Field of Classification Search
None
See application file for complete search history.

(56) References Cited

U.S. PATENT DOCUMENTS

| | | | | |
|---|---|---|---|---|
| 9,989,541 | B2* | 6/2018 | Shi | G01N 33/6896 |
| 2007/0020637 | A1* | 1/2007 | Isogai | C07K 14/47 |
| | | | | 435/6.16 |
| 2012/0315630 | A1* | 12/2012 | Gong | C12Q 1/6827 |
| | | | | 435/6.11 |
| 2013/0065825 | A1* | 3/2013 | Greco | A61K 38/2264 |
| | | | | 514/5.8 |
| 2013/0079834 | A1* | 3/2013 | Levine | A61N 1/36053 |
| | | | | 607/3 |
| 2016/0305962 | A1* | 10/2016 | Shi | G01N 33/6896 |

OTHER PUBLICATIONS

Wilderman et al., Role of PACAP in the relationship between cAMP and opioids in hypoxia-induced pial artery vasodilation, Mar. 1997, American Journal of Physiology 272(3, pt 2): H1350-H1358.*

* cited by examiner

*Primary Examiner* — John D Ulm

(57) ABSTRACT

Described herein are methods, systems and compositions for the diagnosis, prognosis and treatment of dementia and Alzheimer's disease. Also described are methods, systems and compositions to distinguish between Alzheimer's disease and Parkinson's disease. In various embodiments levels of PACAP and/or SIRT3 are analyzed for the diagnosis, prognosis and treatment of dementia and Alzheimer's disease.

18 Claims, 5 Drawing Sheets

DIAGNOSING AND TREATING ALZHEIMERS DISEASE

CROSS REFERENCE TO RELATED APPLICATIONS

This application is a continuation of U.S. patent application Ser. No. 15/103,059, filed Jun. 9, 2016, currently pending, which is a National Phase of International Application No. PCT/US2014/072216, filed Dec. 23, 2014, now expired, which claimed priority under 35 U.S.C. § 119(e) to U.S. Provisional Patent Application No. 61/921,359, filed Dec. 27, 2013, now expired, the contents of which are herein incorporated by reference in their entirety.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Pituitary Adenylate Cyclase Activating Polypeptide (PACAP), as a small peptide with either 38 amino acids in full length form (PACAP-38), or 27 amino acids in short form (PACAP-27), is broadly recognized as a neurotrophin associated with stress. Both forms strongly increase cyclic adenosine monophosphate (cAMP) by activating adenylate cyclase, and hence named as PACAP. Subsequent research showed that PACAP is not only an endocrine hormone, but intrinsically expressed in multiple brain regions and peripheral tissues. PACAP is a potent neurotrophic and neuroprotective peptide in the central nervous system (CNS). PACAP-38 is the major form in brain, while PACAP-27 exists in minor quantity. Both forms of PACAP bind to and activate G protein-coupled receptors (PAC1, VPAC1, and VPAC2). PAC1 is mainly localized in the CNS; while VPAC1 and VPAC2 are in the vascular system and the gastrointestinal tract.

PACAP has been shown to promote synaptic transmission, long term potentiation and memory under physiological conditions. However, the relevance of PACAP expression has not been extensively studied in the human brain, including those suffering from Alzheimer's disease (AD), a progressive mental deterioration and form of dementia that often occurs in old age due to generalized degeneration of the brain. AD is a neurodegenerative disorder that affects memory and other cognitive functions, and is the most common cause of dementia. Alzheimer's Disease Association (ADA) survey shows that 5.4 million people in the United States (US) currently have AD and 13.5 million are expected to have AD within the next 40 years. AD affects over 26 million people worldwide and currently there is no cure for the disease. With the growing number of people living to older ages, there is an urgency to better understand elements of the pathogenic pathway, discover agents that target these elements, and establish their roles in the treatment and prevention of AD. But effective biomarkers and treatment are lacking. There is no disease modifying medication available on the market.

Thus, there is a need in the art for novel and effective treatments and methods of diagnosing Alzheimer's disease and other forms of dementia.

SUMMARY OF THE INVENTION

The following embodiments and aspects thereof are described and illustrated in conjunction with compositions and methods which are meant to be exemplary and illustrative, not limiting in scope.

Various embodiments of the present invention provide for a method of diagnosing dementia and/or a neurological condition in an individual, comprising: obtaining a sample from the individual; preparing the sample to be assayed by a serological test to determine the presence or absence of low SIRT3 expression levels and/or low PACAP expression levels; and diagnosing dementia and/or a neurological condition based on the presence of low SIRT3 expression levels and/or low PACAP expression levels relative to those levels found in a healthy subject.

In various embodiments, the sample to be assayed by a serological test can be prepared to determine the presence or absence of low PACAP expression, and dementia and/or a neurological condition can be diagnosed based on the presence of low PACAP expression levels relative to those levels found in a healthy subject.

In various embodiments, the sample to be assayed by a serological test can be prepared to determine the presence or absence of low SIRT3 expression, and dementia and/or a neurological condition can be diagnosed based on the presence of low SIRT3 expression levels relative to those levels found in a healthy subject.

In various embodiments, the dementia can be Alzheimer's disease (AD).

Various embodiments provide for a method for determining whether a subject has dementia and/or a neurological condition, comprising: obtaining a biological sample from a subject; determining the PACAP expression level and/or the SIRT3 expression level in the biological sample; and diagnosing the subject as having dementia if low PACAP expression levels and/or low SIRT3 expression levels relative to a PACAP reference value and/or SSIRT3 reference value is found in the biological sample.

In various embodiments, determining the PACAP expression level or assaying the biological sample to determine PACAP expression level can comprise contacting the biological sample with an anti-PACAP antibody and detecting whether binding occurs or the amount of binding occurring between PACAP protein and the anti-PACAP antibody.

In various embodiments, determining the SIRT3 expression level or assaying the biological sample to determine SIRT3 expression level can comprise contacting the biological sample with an anti-SIRT3 antibody and detecting whether binding occurs or the amount of binding occurring between SIRT3 protein and the anti-SIRT3 antibody.

Various embodiments provide for a method of distinguishing between Alzheimer's disease and Parkinson's disease, comprising: obtaining a biological sample from a subject desiring a distinction between Alzheimer's disease and Parkinson's disease; assaying the biological sample to determine PACAP expression level; and determining the subject has Alzheimer's disease if the PACAP expression level is lower than a reference value, or determining the subject does not have Alzheimer's disease if the PACAP expression level is not lower than the reference value.

In various embodiments, the method can further comprise assaying the biological sample to determine SIRT3 expression level; and determining the subject has Alzheimer's disease if the PACAP expression level and the SIRT3 expression level are lower than their reference values, or determining the subject does not have Alzheimer's disease if the PACAP expression level and the SIRT3 expression level are not lower than their reference values.

Various embodiments provide for a method of prognosing dementia and/or a neurological condition in an individual, comprising: obtaining a sample from the individual; preparing the sample to be assayed by a serological test to determine the presence or absence of low PACAP expression levels and/or low SIRT3 expression levels; and prognosing a severe form of dementia and/or a neurological condition based on the presence of low PACAP expression levels and/or low SIRT3 expression levels relative to those levels found in a healthy subject.

In various embodiments, the sample to be assayed by a serological test can be prepared to determine the presence or absence of low PACAP expression, and a severe form of dementia and/or a neurological condition can be prognosed based on the presence of low PACAP expression levels relative to those levels found in a healthy subject.

In various embodiments, the sample to be assayed by a serological test can be prepared to determine the presence or absence of low SIRT3 expression, and a severe form of dementia and/or a neurological condition can be prognosed based on the presence of low SIRT3 expression levels relative to those levels found in a healthy subject.

In various embodiments, the dementia is Alzheimer's disease (AD).

Various embodiments provide for a method of diagnosing susceptibility to Alzheimer's disease, comprising: obtaining a sample from the individual; preparing the sample to be assayed by a serological test to determine the presence or absence of low SIRT3 and/or PACAP expression levels; and diagnosing susceptibility to Alzheimer's disease based on the presence of low SIRT3 and/or PACAP expression levels relative to those levels found in a healthy subject.

In various embodiments, the sample to be assayed by a serological test can be prepared to determine the presence or absence of low SIRT3 expression, and the individual can be diagnosed to be susceptible to Alzheimer's disease based on the presence of low SIRT3 expression levels relative to those levels found in a healthy subject.

In various embodiments, the sample to be assayed by a serological test can be prepared to determine the presence or absence of low PACAP expression, and the individual can be diagnosed to be susceptible to Alzheimer's disease based on the presence of low PACAP expression levels relative to those levels found in a healthy subject.

Various embodiments provide for a method of diagnosing susceptibility to a neurological disorder, comprising: obtaining a sample from the individual; preparing the sample to be assayed by a serological test to determine the presence or absence of low SIRT3 and/or PACAP expression levels; and diagnosing susceptibility to the neurological disorder based on the presence of low SIRT3 and/or PACAP expression levels relative to those levels found in a healthy subject.

In various embodiments, the sample to be assayed by a serological test can be prepared to determine the presence or absence of low PACAP expression, and the individual can be diagnosed to be susceptible to the neurological disorder based on the presence of low PACAP expression levels relative to those levels found in a healthy subject.

In various embodiments, the sample to be assayed by a serological test can be prepared to determine the presence or absence of low SIRT3 expression, and the individual can be diagnosed to be susceptible to the neurological disorder based on the presence of low SIRT3 expression levels relative to those levels found in a healthy subject.

A method of treating dementia and/or a neurological condition in an individual, comprising: providing a composition comprising PACAP, SIRT3, salts thereof, analogs thereof, derivatives thereof, pharmaceutical equivalents thereof, or combinations thereof; and administering a therapeutically effective dosage of the composition to the individual.

In various embodiments, the composition can be administered to the individual intravenously.

In various embodiments, the dementia can be Alzheimer's disease (AD).

Various embodiments provide for a method of treating dementia and/or a neurological condition, comprising: providing a composition comprising one or more agonists of receptors to PACAP, SIRT3, or combinations thereof, and administering a therapeutically effective dosage of the composition to the individual. In various embodiments, the dementia is Alzheimer's disease.

Various embodiments provide for a method of treating dementia and/or neurological condition, comprising: providing a composition comprising one or more neurotrophins; and administering a therapeutically effective dosage of the composition to a subject who has been determined to have dementia and/or the neurological condition based on the subject's PACAP level and/or SIRT3 level.

Various embodiments provide for a method for treating dementia and/or neurological condition in a subject, comprising: analyzing a biological sample from the subject for a PACAP level; and administering a neurotrophin or an agonist of a neurotrophin to the subject when the PACAP level is below a reference value to treat dementia and/or neurological condition.

In various embodiments, the method can further comprise: analyzing the biological sample for a SIRT3 level and the neurotrophin or the agonist of a neurotrophin can be administered to the subject when the PACAP level is below a PACAP reference value and the SIRT3 level is below a SIRT3 reference value to treat dementia and/or neurological condition.

Various embodiments provide for a method for treating dementia and/or neurological condition in a subject, comprising: obtaining the results of an analysis of a PACAP level in a subject; and administering a neurotrophin or an agonist of a neurotrophin to the subject when the PACAP level is below a reference value.

In various embodiments, the method can further comprise obtaining the results of an analysis a SIRT3 level and the neurotrophin or the agonist of the neurotrophin can be administered to the subject when the PACAP level is below a PACAP reference value and the SIRT3 level is below a SIRT3 reference value to treat dementia and/or neurological condition.

Various embodiments provide for a method for treating dementia and/or neurological condition in a subject who has been determined to have a PACAP level below a reference value, comprising: administering a neurotrophin or an agonist thereof to the subject. In various embodiments, the subject has also been determined to have a SIRT3 level below a SIRT3 reference value.

Various embodiments provide for a method for treating dementia and/or neurological condition in a subject, comprising: analyzing a biological sample from the subject for a SIRT3 level; and administering a SIRT3 or an agonist thereof to the subject when the SIRT3 level is below a reference value to treat dementia and/or neurological condition.

Various embodiments provide for a method for treating dementia and/or neurological condition in a subject, comprising: obtaining the results of an analysis of a SIRT3 level in a subject; and administering SIRT3 or an agonist thereof to the subject when the SIRT3 level is below a reference value.

Various embodiments provide for a method for treating dementia and/or neurological condition in a subject who has been determined to have a SIRT3 level below a reference value, comprising: administering SIRT3 or an agonist thereof to the subject.

Various embodiments provide for a method of selecting a treatment for dementia and/or neurological condition in a subject, comprising: analyzing a biological sample from the subject for PACAP level and/or SIRT3 level; and prescribing PACAP, SIRT3, agonists thereof, salts thereof, or derivatives thereof, for the subject when the PACAP level is below a PACAP reference value and/or the SIRT3 level is below the SIRT3 reference value.

Various embodiments provide for a composition, comprising: PACAP, SIRT3, an agonists of a receptor to PACAP, an agonist of a receptor to SIRT3, salts thereof, derivatives thereof, or pharmaceutical equivalents thereof, or combinations thereof; and an pharmaceutically acceptable carrier.

Other features and advantages of the invention will become apparent from the following detailed description, taken in conjunction with the accompanying drawings, which illustrate, by way of example, various features of embodiments of the invention.

BRIEF DESCRIPTION OF THE FIGURES

Exemplary embodiments are illustrated in referenced figures. It is intended that the embodiments and figures disclosed herein are to be considered illustrative rather than restrictive.

FIGS. 1A-1D. PACAP level in AD brains were analyzed for correlation with amyloid plaque quantity (indicated by CERAD Plaque score). PACAP levels were inversely correlated with CERAD in the ENT (Pearson r=−0.6764, $p<0.05$, FIG. 1A) and SFG (Pearson r=−0.7088, $p<0.05$, FIG. 1C) but not in the MTG (FIG. 1B) or PVC (FIG. 1D). PACAP level was quantified by ELISA and normalized with total protein (mg) of the brain tissue. FIG. 1E. PACAP level in CSF was quantified and correlated with tau pathology (indicated by Braak Stage). All CN cases were in Stage III-IV. Four AD cases were in Stage III-IV while the other 5 AD cases in Stage V-VI. PACAP was lower in advanced Braak Stage V-VI than that in moderate Braak Stage III-IV ($p<0.05$). PACAP level was quantified by ELISA and normalized with CSF volume (ml). ENT=Entorhinal Cortex, MTG=Middle Temporal Lobe, SFG=Superior Frontal Cortex, PVC=Primary Visual Cortex, AD=Alzheimer's disease (blue dot), CN=cognitively normal controls (black dot).

FIG. 2A. PACAP was reduced in AD but not in PDD or FTLD. FIG. 2B. PACAP is correlated with the Z score of DRS. CN and AD cases were separated by the dotted line based on their DRS score. AD=Alzheimer's disease, CN=cognitively normal controls, PDD=Parkinson Disease with Dementia, FTLD=Frontotemporal Lobe Dementia, DRS=Dementia Rating Scale-Revised (DRS-R), a global cognitive assessment. * indicates $p<0.05$ and ** $p<0.01$.

FIG. 3A: PACAP in CSF was expressed as ng PACAP per ml CSF. FIG. 3B: PACAP in SFG. FIG. 3C: PACAP in MTG. FIG. 3D: PACAP in PVC. In FIGS. 3B, 3C, and 3D, PACAP was expressed as ng PACAP per mg protein from the same sample. Bars indicate standard errors. One way ANOVA with Post hoc Tukey test. * indicates $p<0.05$,  $p<0.01$, *$p<0.001$.

FIG. 5A. PAC1 receptor quantification in SFG, * indicate $p<0.05$, one way ANOVA with post hoc Tukey's tests. FIG. 5B. PAC1 receptor quantification in MTG. FIG. 5C. PAC1 receptor quantification in MTG. FIG. 5D. Pharmacodynamic model fit of SFG PACAP and SFG PAC1 level to predict the correlation with Stroop Color-Word Interference z scores. The dashed line marks the point at significant correlation ($p<0.05$). FIG. 5E. Pharmacodynamic model fit of MTG PACAP and MTG PAC1 levels to predict the correlation with AVLT scores. The dashed line marks the point at significant correlation ($p<0.05$).

DESCRIPTION OF THE INVENTION

Figure 1A:
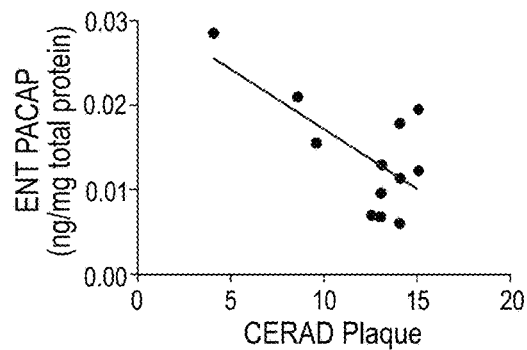
FIGS. 1A-1E depict, in accordance with embodiments herein, PACAP levels are inversely related to AD pathology.
Figure 1C:
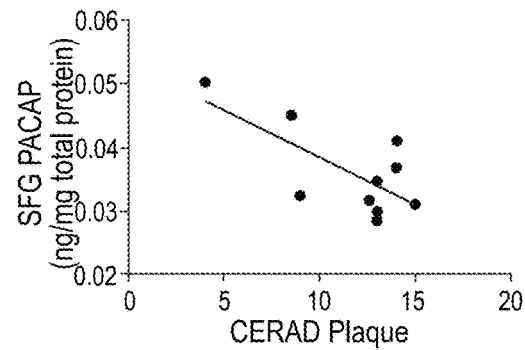
Figure 1B:
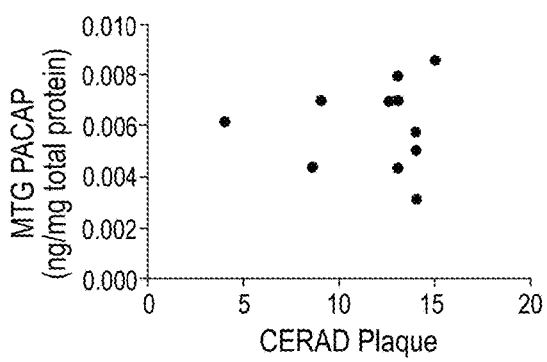
Figure 1D:
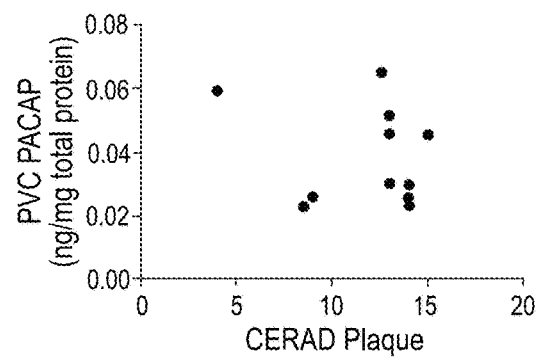

All references cited herein are incorporated by reference in their entirety as though fully set forth. Unless defined otherwise, technical and scientific terms used herein have the same meaning as commonly understood by one of ordinary skill in the art to which this invention belongs. Hornyak, et al., Introduction to Nanoscience and Nanotechnology, CRC Press (2008); Singleton et al., Dictionary of Microbiology and Molecular Biology 3rd ed., J. Wiley & Sons (New York, N.Y. 2001); March, Advanced Organic Chemistry Reactions, Mechanisms and Structure 7th ed., J. Wiley & Sons (New York, N.Y. 2013); and Sambrook and Russel, Molecular Cloning: A Laboratory Manual 4th ed., Cold Spring Harbor Laboratory Press (Cold Spring Harbor, N.Y. 2012), provide one skilled in the art with a general guide to many of the terms used in the present application. One skilled in the art will recognize many methods and materials similar or equivalent to those described herein, which could be used in the practice of the present invention. Indeed, the present invention is in no way limited to the methods and materials described.

As used herein, "PACAP" is an abbreviation of Pituitary Adenylate Cyclase Activating Polypeptide.

As used herein, "AD" is an abbreviation of Alzheimer's disease.

As used herein, "SIRT" is an abbreviation of sirtuin.

As used herein, "analog" of a molecule such as a peptide refers to a molecule similar in function to either the entire molecule or to a fragment thereof. Analogs typically differ from naturally occurring peptides at one or a few positions, often by virtue of conservative substitutions. Analogs typically exhibit at least 80 or 90% sequence identity with natural peptides. Some analogs also include unnatural amino acids or modifications of N or C terminal amino acids. Examples of unnatural amino acids are, for example but not limited to; disubstituted amino acids, N-alkyl amino acids, lactic acid, 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine. Fragments and analogs can be screened for prophylactic or therapeutic efficacy in transgenic animal models.

As used herein, "conservative amino acid substitutions" result from replacing one amino acid with another having similar structural and/or chemical properties, such as the replacement of a leucine with an isoleucine or valine, an aspartate with a glutamate, or a threonine with a serine. Thus, a "conservative substitution" of a particular amino acid sequence refers to substitution of those amino acids that are not critical for polypeptide activity or substitution of amino acids with other amino acids having similar properties (e.g., acidic, basic, positively or negatively charged, polar or non-polar, etc.) such that the substitution of even critical amino acids does not reduce the activity of the peptide, (e.g., the ability of the peptide to penetrate the blood brain barrier (BBB)). Conservative substitution tables providing functionally similar amino acids are well known in the art. For example, the following six groups each contain amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W). In some embodiments, individual substitutions, deletions or additions that alter, add or delete a single amino acid or a small percentage of amino acids can also be considered "conservative substitutions" if the change does not reduce the activity of the peptide. Insertions or deletions are typically in the range of about 1 to 5 amino acids. The choice of conservative amino acids may be selected based on the location of the amino acid to be substituted in the peptide, for example if the amino acid is on the exterior of the peptide and expose to solvents, or on the interior and not exposed to solvents.

In alternative embodiments, one can select the amino acid which will substitute an existing amino acid based on the location of the existing amino acid, i.e., its exposure to solvents (i.e., if the amino acid is exposed to solvents or is present on the outer surface of the peptide or polypeptide as compared to internally localized amino acids not exposed to solvents). Selection of such conservative amino acid substitutions are well known in the art, for example as disclosed in Dordo et al, J. Mol Biol, 1999, 217, 721-739 and Taylor et al, J. Theor. Biol. 119(1986); 205-218 and S. French and B. Robson, J. Mol. Evol. 19(1983)171. Accordingly, one can select conservative amino acid substitutions suitable for amino acids on the exterior of a protein or peptide (i.e., amino acids exposed to a solvent), for example, but not limited to, the following substitutions can be used: substitution of Y with F, T with S or K, P with A, E with D or Q, N with D or G, R with K, G with N or A, T with S or K, D with N or E, I with L or V, F with Y, S with T or A, R with K, G with N or A, K with R, A with S, K or P.

In alternative embodiments, one can also select conservative amino acid substitutions encompassed suitable for amino acids on the interior of a protein or peptide, for example one can use suitable conservative substitutions for amino acids is on the interior of a protein or peptide (i.e. the amino acids are not exposed to a solvent).

As used herein, "derivative" refers to peptides which have been chemically modified, for example but not limited to by techniques such as ubiquitination, labeling, pegylation (derivatization with polyethylene glycol), lipidation, glycosylation, or addition of other molecules. A molecule also a "derivative" of another molecule when it contains additional chemical moieties not normally a part of the molecule. Such moieties can improve the molecule's solubility, absorption, biological half-life, etc. The moieties can alternatively decrease the toxicity of the molecule, eliminate or attenuate any undesirable side effect of the molecule, etc.

As further described herein, Pituitary Adenylate Cyclase Activating Polypeptide (PACAP) is a neurotrophin. The inventors studied the brains of pathologically confirmed late onset AD patients and age matched cognitively normal (CN) subjects to investigate the expression of PACAP mRNA (34 AD and 14 CN) and protein (12 AD and 11 CN). They found that PACAP levels are reduced in multiple brain regions, including the entorhinal cortex (ENT), the middle temporal gyrus (MTG), the superior frontal gyrus (SFG) and the primary visual cortex (PVC). This reduction is inversely correlated with amyloid burden (CERAD plaque density) in the ENT and SFG but not the PVC, a region spared in most cases of AD. PACAP expression is lower in the advanced Braak Stage (V-VI) than that in the moderate stage (III-IV). PACAP level is correlated with Dementia Rating Scale, a global cognitive assessment. Furthermore, PACAP level in cerebrospinal fluid reflects its level in the brain and is reduced in AD but not in Parkinson's disease dementia or Frontotemporal lobe dementia. The close inverse relationship between PACAP reduction and AD pathological markers suggests that down regulation of PACAP contributes to AD pathogenesis.

Further, AD is associated with a characteristic and progressive pattern of reductions in regional cerebral metabolism as measured by flourodeoxyglucose positron emission tomography (FDG PET). These reductions begin years before the onset of cognitive symptoms and are correlated with clinical severity. Evidence supports the possibility that mitochondrial dysfunction is an initiating factor leading to apoptosis which is a common pathological mechanism for neurodegeneration. Insufficient energy metabolism due to complex I malfunction may contribute to tau phosphorylation, a crucial pathological step in Alzheimer's disease. PACAP and Sirts target mitochondria to improve its function. In addition, PACAP and Sirt 3 have a direct protective effect on neurons, likely targeting on intrinsic apoptotic pathway. The inventors found that PACAP and SIRT3 expression is reduced in AD patients and the triple transgenic mouse model of AD. PACAP and SIRT3 protects against Aβ induced cell death by enhancing mitochondrial function. In one embodiment, PACAP and SIRT3, individually and/or collectively, can be used as a biomarker for AD. In another embodiment, PACAP and SIRT3, individually and/or collectively, may be used as a treatment for AD. In another embodiment, PACAP and/or SIRT3 will improve mitochondria function. In another embodiment, PACAP and/or SIRT3 will rescue neurons from apoptosis.

We show that PACAP levels start to decline before the onset of AD, as early as the MCI stage. This reduction in PACAP is region specific, targeting vulnerable regions of AD. These data support the possibility that the PACAP deficit is a risk factor for AD pathogenesis. Furthermore, the PACAP deficit in selected cerebral regions may predict region-specific cognitive function deterioration. We have found the strongest correlation between PACAP levels and cognitive performance in SFG and MTG, two regions heavily involved in AD pathology, and both of which represent cognitive abilities that are affected early in the course of AD. The CSF PACAP level inversely correlates with the total quantities of amyloid plaques and tangle plaques. PACAP specific receptor PAC1 showed a transient upregulation in the frontal lobe of MCI subjects but not in AD patients, suggesting a potential compensatory mechanism in MCI. AD patients may lose this compensatory capability as the disease progresses.

Using ligand-receptor pharmacodymamic model, we estimated that an approximate 1:1-2:1 ratio of PACAP:PAC1 in SFG predicts the Stroop Color-Word Interference task performance. In the temporal lobe however, PACAP has to be excessive (~5 fold) to reach a significant correlation with cognitive performance. This is consistent with our data that shows lower levels of PAC1 receptor in MTG compared to SFG. An alternative explanation is that a large proportion of measured PACAP in MTG is intracellularly retained and unavailable for paracrine secretion, as our measurement did not discern multiple compartments in tissues; or there is another subtype of PAC1 that has weak ligand-receptor interaction in this region. Taken together, the action target of PACAP is predominantly localized in the frontal lobe. This MTG-SFG pathway is consistent with the proposed neurodegenerative network most affected in AD.

The PACAP level in SFG is higher than that of MTG regardless in controls, MCIs or AD patients. But the PACAP deficit in AD is more severe in MTG (~60% reduction) than in SFG (45% reduction). Interestingly, the total Aβ in SFG was increased 10 fold in AD compared to the control, whereas Aβ in MTG was increased 100 fold in AD. This regional difference in Aβ deposition is consistent with the inverse relationship between PACAP and amyloid load, as shown herein.

Although the human studies on PACAP are in the preliminary stage, animal studies have shown beneficial effects of PACAP on cognition and memory. The earliest clue of PACAP's effects on memory came from amnesiac (amn) gene mutant flies. Amn gene encodes a homolog of vertebral PACAP. PACAP is also essential for associative memory in Lymnaea stagnalis, a prototype model for studying the molecular mechanism of simple associative learning. Most importantly, intranasal administration of PACAP enhances Novel object recognition in SAMP8 mice and APP transgenic mice. The memory enhancing effect of PACAP may be mediated by multiple molecular mechanisms, including enhancing inward currents through NMDA channel and AMPA channel, inhibiting HCN channel or A-type K channel.

Various embodiments of the present invention are based, at least in part, on these findings.

Diagnosis of Dementia and Neurological Conditions

In various embodiments, the present invention provides a method of diagnosing dementia and/or a neurological condition in an individual by obtaining a sample from the individual, preparing the sample to be assayed by a serological test to determine the presence or absence of PACAP expression levels, and diagnosing dementia and/or a neurological condition based on the presence of low PACAP expression levels relative to those levels found in a healthy subject. In various embodiments, the method further comprises preparing the sample to be assayed by a serological test to determine the presence or absence of SIRT3 expression levels, and diagnosing dementia and/or a neurological condition based on the presence of low PACAP expression levels and low SIRT3 expression levels relative to those levels found in a healthy subject Various embodiments of the present invention provides for a method for determining whether a subject has dementia, comprising: obtaining a biological sample from a subject; determining the PACAP expression level in the biological sample, and diagnosing the subject as having dementia if low PACAP expression levels relative to a reference value is found in the biological sample. In various embodiments, the method further comprises determining the SIRT3 expression level in the biological sample, and diagnosing the subject as having dementia if low PACAP expression levels and low SIRT3 expression levels relative to a reference value are found in the biological sample Various embodiments of the present invention provides for a method for determining whether a subject has a neurological condition, comprising: obtaining a biological sample from a subject; determining the PACAP expression level in the biological sample, and diagnosing the subject as having the neurological condition if low PACAP expression levels relative to a reference value is found in the biological sample. In various embodiments, the method further comprises determining the SIRT3 expression level in the biological sample, and diagnosing the subject as having the neurological condition if low PACAP expression levels and low SIRT3 expression levels relative to a reference value are found in the biological sample Various embodiments provide for a method of diagnosing dementia comprising obtaining a biological sample from a subject desiring a diagnosis regarding dementia; assaying the biological sample to determine PACAP expression level; and determining the subject has dementia if the PACAP expression level is lower than a reference value, or determining the subject does not have dementia if the PACAP expression level is not lower than the reference value. In various embodiments, the method further comprises assaying the biological sample to determine SIRT3 expression level; and determining the subject has dementia if the PACAP expression level and the SIRT3 expression level are lower than their reference values, or determining the subject does not have dementia if the PACAP expression level and the SIRT3 expression level are not lower than their reference values.

In various embodiments, the present invention provides for a method of diagnosing dementia and/or a neurological condition in an individual by obtaining a sample from the individual, preparing the sample to be assayed by a serological test to determine the presence or absence of SIRT3 expression levels, and diagnosing dementia and/or a neurological condition based on the presence of low SIRT3 expression levels relative to those levels found in a healthy subject.

Various embodiments of the present invention provides for a method for determining whether a subject has dementia, comprising: obtaining a biological sample from a subject; determining the SIRT3 expression level in the biological sample, and diagnosing the subject as having dementia if low SIRT3 expression levels relative to a reference value is found in the biological sample.

Various embodiments of the present invention provides for a method for determining whether a subject has a neurological condition, comprising: obtaining a biological sample from a subject; determining the SIRT3 expression level in the biological sample, and diagnosing the subject as having the neurological condition if low SIRT3 expression levels relative to a reference value is found in the biological sample.

Various embodiments provide for a method of diagnosing dementia comprising obtaining a biological sample from a subject desiring a diagnosis regarding dementia; assaying the biological sample to determine SIRT3 expression level; and determining the subject has dementia if the SIRT3 expression level is lower than a reference value, or determining the subject does not have dementia if the SIRT3 expression level is not lower than the reference value.

Various embodiments provide for a method of diagnosing a neurological condition comprising obtaining a biological sample from a subject desiring a diagnosis regarding dementia; assaying the biological sample to determine SIRT3 expression level; and determining the subject has the neurological condition if the SIRT3 expression level is lower than a reference value, or determining the subject does not have the neurological condition if the SIRT3 expression level is not lower than the reference value.

In various embodiments, the invention provides for a system for diagnosing dementia and/or neurological condition in a subject, comprising: a biological sample from the subject; an antibody that specifically binds to PACAP and/or an antibody that specifically binds to SIRT3; and a machine to detect the binding of the antibody PACAP and/or the antibody to SIRT3.

In various embodiments, the invention provides for a composition for diagnosing dementia and/or neurological condition in a subject, comprising: a biological sample obtained from the subject; and an antibody that specifically binds to PACAP and/or an antibody that specifically binds to SIRT3.

In various embodiments, the invention provides for a system for diagnosing dementia and/or neurological condition in a subject, comprising: an antibody-PACAP complex and/or an antibody-SRIT3 complex in a biological sample obtained from the subject; and a machine to detect the antibody-PACAP complex and/or an antibody-SIRT3 complex.

In various embodiments, the invention provides for a composition for diagnosing dementia and/or neurological condition in a subject, comprising: an antibody-PACAP complex and/or an antibody-SRIT3 complex in a biological sample obtained from the subject.

In various embodiments, PACAP is the full length form (PACAP-38). In various embodiments, PACAP is the short form (PACAP-27). In other embodiments, PACAP is both the full length form and the short form.

In various embodiments, the dementia is Alzheimer's disease (AD). In various embodiments, the individual or subject is human.

Prognosis of Dementia and Neurological Conditions

In various embodiments, the present invention provides a method of prognosing dementia and/or a neurological condition in an individual by obtaining a sample from the individual, preparing the sample to be assayed by a serological test to determine the presence or absence of PACAP expression levels, and prognosing a severe form of dementia and/or a neurological condition based on the presence of low PACAP expression levels relative to those levels found in a healthy subject. In various embodiments, the method further comprises preparing the sample to be assayed by a serological test to determine the presence or absence of SIRT3 expression levels, and prognosing a severe form of dementia and/or a neurological condition based on the presence of low PACAP expression levels and low SIRT3 expression levels relative to those levels found in a healthy subject. In another embodiment, the dementia is Alzheimer's disease (AD). In another embodiment, the individual is human.

In another embodiment, the present invention provides a method of prognosing dementia and/or a neurological condition in an individual by obtaining a sample from the individual, preparing the sample to be assayed by a serological test to determine the presence or absence of SIRT3 expression levels, and prognosing a severe form of dementia and/or a neurological condition based on the presence of low SIRT3 expression levels relative to those levels found in a healthy subject. In another embodiment, the dementia is Alzheimer's disease (AD). In another embodiment, the individual is human.

Various embodiments of the present invention provides for a method for prognosing dementia, comprising: obtaining a biological sample from a subject; determining the PACAP expression level in the biological sample, and prognosing the subject as having a severe form of dementia if low PACAP expression levels relative to a reference value is found in the biological sample. In various embodiments, the method further comprises determining the SIRT3 expression level in the biological sample, and prognosing the subject as having a severe form of dementia if low PACAP expression levels and low SIRT3 expression levels relative their reference values are found in the biological sample.

Various embodiments of the present invention provides for a method for prognosing a neurological condition, comprising: obtaining a biological sample from a subject; determining the PACAP expression level in the biological sample, and prognosing the subject as having a severe form of the neurological condition if low PACAP expression levels relative to a reference value is found in the biological sample. In various embodiments, the method further comprises determining the SIRT3 expression level in the biological sample, and prognosing the subject as having a severe form of the neurological condition if low PACAP expression levels and low SIRT3 expression levels relative to their reference values are found in the biological sample.

In various embodiments, PACAP is the full length form (PACAP-38). In various embodiments, PACAP is the short form (PACAP-27). In other embodiments, PACAP is both the full length form and the short form.

Distinguishing Between of Alzheimer's Disease and Parkinson's Disease

Various embodiments of the present invention provides for a method for distinguishing whether a subject has Alzheimer's disease or Parkinson's disease, comprising: obtaining a biological sample from a subject; determining the PACAP expression level in the biological sample, and diagnosing the subject as having Alzheimer's disease if low PACAP expression levels relative to a reference value is found in the biological sample. In various embodiments, the method further comprises determining the SIRT3 expression level in the biological sample, and diagnosing the subject as having Alzheimer's disease if low PACAP expression levels and low SIRT3 expression levels relative to a reference value are found in the biological sample.

Various embodiments provide for a method of distinguishing between Alzheimer's disease and Parkinson's disease comprising obtaining a biological sample from a subject desiring a distinction between Alzheimer's disease and Parkinson's disease; assaying the biological sample to determine PACAP expression level; and determining the subject has Alzheimer's disease if the PACAP expression level is lower than a reference value, or determining the subject does not have Alzheimer's disease if the PACAP expression level is not lower than the reference value. In various embodiments, the method further comprises assaying the biological sample to determine SIRT3 expression level; and determining the subject has Alzheimer's disease if the PACAP expression level and the SIRT3 expression level are lower than their reference values, or determining the subject does not have Alzheimer's disease if the PACAP expression level and the SIRT3 expression level are not lower than their reference values.

In various embodiments, the individual or subject is human.

In various embodiments, PACAP is the full length form (PACAP-38). In various embodiments, PACAP is the short form (PACAP-27). In other embodiments, PACAP is both the full length form and the short form.

Treatment of Dementia and Neurological Conditions

In another embodiment, the present invention provides a method of treating dementia and/or a neurological condition in an individual by providing a composition comprising SIRT3, or a salt, analog, derivative, pharmaceutical equivalent thereof, and administering a therapeutically effective dosage of the composition to the individual. In another embodiment, the composition is administered to the individual intravenously. In another embodiment, the composition is administered intranasally. In another embodiment, the dementia is Alzheimer's disease (AD). In another embodiment, the individual is human.

In another embodiment, the present invention provides a method of treating dementia and/or a neurological condition by providing a composition comprising one or more agonists of receptors to PACAP or SIRT3, and administering a therapeutically effective dosage of the composition to the individual. In another embodiment, the dementia is Alzheimer's disease.

In various embodiments, the present invention provides a method of treating dementia and/or neurological condition in an individual by administering a therapeutically effective dosage of a composition comprising one or more neurotrophins to the individual.

In various embodiments, the present invention provides a method of treating dementia and/or neurological condition, comprising administering a therapeutically effective dosage of a composition comprising one or more neurotrophins to a subject who has been determined to have dementia and/or the neurological condition by a method of the present invention.

In various embodiments, the present invention provides a method of treating dementia and/or neurological condition, comprising providing a composition comprising one or more neurotrophins; and administering a therapeutically effective dosage of the composition to a subject who has been determined to have dementia and/or the neurological condition by a method of the present invention.

In various embodiments, the present invention provides for a method for treating dementia and/or neurological condition in a subject, comprising: analyzing a biological sample from the subject for a PACAP level; and administering a neurotrophin or an agonist of a neurotrophin to the subject when the PACAP level is below a reference value to treat dementia and/or neurological condition. In various embodiments, the method further comprises analyzing the biological sample for a SIRT3 level and a neurotrophin or an agonist of a neurotrophin is administered to the subject when the PACAP level is below a PACAP reference value and the SIRT3 level is below a SIRT3 reference value to treat dementia and/or neurological condition.

In various embodiments, the present invention provides for a method for treating dementia and/or neurological condition in a subject, comprising: obtaining the results of an analysis of a PACAP level in a subject; and administering a neurotrophin or an agonist of a neurotrophin to the subject when the PACAP level is below a reference value. In various embodiments, the method further comprises obtaining the results of an analysis a SIRT3 level and the neurotrophin or an agonist of the neurotrophin is administered to the subject when the PACAP level is below a PACAP reference value and the SIRT3 level is below a SIRT3 reference value to treat dementia and/or neurological condition.

In various embodiments, the present invention provide for a method for treating dementia and/or neurological condition in a subject who has been determined to have a PACAP level below a reference value, comprising: administering a neurotrophin or an agonist thereof to the subject. In various embodiments, the subject has also been determined to have a SIRT3 level below a SIRT3 reference value.

In various embodiments, the present invention provides for a method for treating dementia and/or neurological condition in a subject, comprising: analyzing a biological sample from the subject for a SIRT3 level; and administering a SIRT3 or an agonist thereof to the subject when the SIRT3 level is below a reference value to treat dementia and/or neurological condition.

In various embodiments, the present invention provides for a method for treating dementia and/or neurological condition in a subject, comprising: obtaining the results of an analysis of a SIRT3 level in a subject; and administering SIRT3 or an agonist thereof to the subject when the SIRT3 level is below a reference value.

In various embodiments, the present invention provide for a method for treating dementia and/or neurological condition in a subject who has been determined to have a SIRT3 level below a reference value, comprising: administering SIRT3 or an agonist thereof to the subject.

In various embodiments, the present invention provides for a method of selecting a treatment for dementia and/or neurological condition in a subject, comprising: analyzing a biological sample from the subject for PACAP level and/or SIRT3 level; and prescribing PACAP, SIRT3, agonists thereof, salts thereof, derivatives thereof, for the subject when the PACAP level is below a PACAP reference value and/or the SIRT3 level is below the SIRT3 reference value.

In various embodiments, the analysis or determination of PACAP and/or SIRT3 levels are done via the methods described herein.

In various embodiments, the neurotrophin includes PACAP, or a salt, derivative, or pharmaceutical equivalent thereof. In another embodiment, the composition is administered intravenously. In various embodiments, PACAP is the full length form (PACAP-38). In various embodiments, PACAP is the short form (PACAP-27). In other embodiments, PACAP is both the full length form and the short form.

In another embodiment, the individual is treated by decreasing amyloid plaque in the individual.

In another embodiment, the dementia is Alzheimer's disease.

Biological Samples

Biological samples used in accordance with various embodiments of the present invention can be mammalian body fluids, sera such as blood (including whole blood as well as its plasma and serum), CSF (spinal fluid), urine, sweat, saliva, tears, pulmonary secretions, breast aspirate, prostate fluid, seminal fluid, stool, cervical scraping, cysts, amniotic fluid, intraocular fluid, mucous, moisture in breath, animal tissue, cell lysates, tumor tissue, hair, skin, buccal scrapings, nails, bone marrow, cartilage, prions, bone powder, ear wax, etc. or even from external or archived sources such as tumor samples (i.e., fresh, frozen or paraffin-embedded). Samples, such as body fluids or sera, obtained during the course of clinical trials may be advantageous for, although samples obtained directly from living subjects under alternate conditions or for other purposes may be readily used as well. In various embodiments, the biological sample is cerebrospinal fluid (CSF). In various embodiments, the biological sample is plasma. In various embodiments, the biological sample is serum.

Reference Values

PACAP Reference Values

In various embodiments, the reference value can be the median or mean ADCYAP1 (the PACAP gene) expression level from a population of subjects with without dementia or the neurological condition.

The nucleic acid samples used to compute a reference value are taken from at least 1, 2, 5, 10, 20, 30, 40, 50, 100, or 200 different organisms of that species. According to certain aspects of the invention, nucleic acid "derived from" genomic DNA, as used in the methods of the invention, e.g., in hybridization experiments to determine ADCYAP1 expression can be fragments of genomic nucleic acid generated by restriction enzyme digestion and/or ligation to other nucleic acid, and/or amplification products of genomic nucleic acids, pre-messenger RNA (pre-mRNA), or post-messenger RNA (the mature form of mRNA), amplification products of pre- or post-mRNA, or genomic DNA fragments grown up in cloning vectors generated, e.g., by "shotgun" cloning methods. In certain embodiments, genomic nucleic acid samples are digested with restriction enzymes.

In various embodiments, the reference value can be the median or mean PACAP protein expression level from a population of subjects with without dementia or the neurological condition.

The protein samples used to compute a reference value are taken from at least 1, 2, 5, 10, 20, 30, 40, 50, 100, or 200 different organisms of that species.

SIRT3 Reference Value

In various embodiments, the reference value can be the median or mean SIRT3 expression level from a population of subjects with without dementia or the neurological condition.

The nucleic acid samples used to compute a reference value are taken from at least 1, 2, 5, 10, 20, 30, 40, 50, 100, or 200 different organisms of that species. According to certain aspects of the invention, nucleic acid "derived from" genomic DNA, as used in the methods of the invention, e.g., in hybridization experiments to determine SIRT3 expression can be fragments of genomic nucleic acid generated by restriction enzyme digestion and/or ligation to other nucleic acid, and/or amplification products of genomic nucleic acids, pre-messenger RNA (pre-mRNA), or post-messenger RNA (the mature form of mRNA), amplification products of pre- or post-mRNA, or genomic DNA fragments grown up in cloning vectors generated, e.g., by "shotgun" cloning methods. In certain embodiments, genomic nucleic acid samples are digested with restriction enzymes.

In various embodiments, the reference value can be the median or mean SIRT3 protein expression level from a population of subjects with without dementia or the neurological condition.

The protein samples used to compute a reference value are taken from at least 1, 2, 5, 10, 20, 30, 40, 50, 100, or 200 different organisms of that species.

Determining Expression Levels and Assays

In various embodiments, determining the PACAP expression level or assaying the biological sample to determine PACAP expression level comprises detecting PACAP (ADCYAP1) mRNA with a polynucleotide capable of hybridizing with PACAP (ADCYAP1) mRNA under stringent hybridization conditions.

In various embodiments, determining the PACAP expression level or assaying the biological sample to determine PACAP expression level (ADCYAP1 expression level) comprises using DNA sequencing, mRNA expression assay, RT-PCR, real-time PCR, or a combination thereof.

In various embodiments, determining the PACAP expression level or assaying the biological sample to determine PACAP expression level comprises contacting the biological sample with an anti-PACAP antibody and detecting whether binding occurs or the amount of binding occurring between PACAP protein and the anti-PACAP antibody. In various embodiments, wherein the anti-PACAP antibody binds to an epitope that is present on PACAP.

In various embodiments, detecting whether binding occurs between PACAP protein and the anti-PACAP antibody comprises using flow cytometry.

In various embodiments, determining the PACAP expression level or assaying the biological sample to determine PACAP expression level comprises detecting a PACAP protein with an antibody capable of specifically binding to a PACAP protein.

In various embodiments, determining the PACAP expression level or assaying the biological sample to determine PACAP expression level comprises using enzyme-linked immunosorbent assay (ELISA), including but not limited to indirect ELISA, sandwich ELISA, competitive ELISA, multiple and portable ELISA.

In various embodiments, determining the PACAP expression level or assaying the biological sample to determine PACAP expression level comprises using immunohistochemistry, flow cytometry, fluorescence in situ hybridization (FISH), radioimmuno assays, and affinity purification.

In various embodiments, determining the SIRT3 expression level or assaying the biological sample to determine SIRT3 expression level comprises detecting SIRT3 mRNA with a polynucleotide capable of hybridizing with SIRT3 mRNA under stringent hybridization conditions.

In various embodiments, determining the SIRT3 expression level or assaying the biological sample to determine SIRT3 expression level comprises using DNA sequencing, mRNA expression assay, RT-PCR, real-time PCR, or a combination thereof.

In various embodiments, determining the SIRT3 expression level or assaying the biological sample to determine SIRT3 expression level comprises contacting the biological sample with an anti-SIRT3 antibody and detecting whether binding occurs or the amount of binding occurring between SIRT3 protein and the anti-SIRT3 antibody. In various embodiments, wherein the anti-SIRT3 antibody binds to an epitope that is present on SIRT3. In various embodiments, detecting whether binding occurs between SIRT3 protein and the anti-SIRT3 antibody comprises using flow cytometry.

In various embodiments, determining the SIRT3 expression level or assaying the biological sample to determine SIRT3 expression level comprises detecting a SIRT3 protein with an antibody capable of specifically binding to a SIRT3 protein.

In various embodiments, determining the SIRT3 expression level or assaying the biological sample to determine SIRT3 expression level comprises using enzyme-linked immunosorbent assay (ELISA), including but not limited to indirect ELISA, sandwich ELISA, competitive ELISA, multiple and portable ELISA.

In various embodiments, determining the SIRT3 expression level or assaying the biological sample to determine SIRT3 expression level comprises using immunohistochemistry, flow cytometry, fluorescence in situ hybridization (FISH), radioimmuno assays, and affinity purification.

In one embodiment, the present invention provides a composition comprising PACAP, or a salt, derivative, or pharmaceutical equivalent thereof, and an acceptable carrier. In another embodiment, the present invention provides a composition comprising SIRT3, or a salt, derivative, or pharmaceutical equivalent thereof, and an acceptable carrier. In another embodiment, the present invention provides a composition comprising PACAP and SIRT3, and an acceptable carrier. In another embodiment, the present invention provides a composition comprising one or more agonists of receptors of PACAP or SIRT3, and an acceptable carrier.

In various embodiments, the present invention provides pharmaceutical compositions including a pharmaceutically acceptable excipient along with a therapeutically effective amount of SIRT3, PACAP, and/or one or more agonists of receptors to SIRT3 or PACAP. "Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients may be solid, liquid, semisolid, or, in the case of an aerosol composition, gaseous.

In various embodiments, the pharmaceutical compositions according to the invention may be formulated for delivery via any route of administration. "Route of administration" may refer to any administration pathway known in the art, including but not limited to aerosol, nasal, oral, transmucosal, transdermal or parenteral. "Parenteral" refers to a route of administration that is generally associated with injection, including intraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions may be in the form of solutions or suspensions for infusion or for injection, or as lyophilized powders.

The pharmaceutical compositions according to the invention can also contain any pharmaceutically acceptable carrier. "Pharmaceutically acceptable carrier", or "acceptable carrier", as used herein refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or a combination thereof. Each component of the carrier must be "pharmaceutically acceptable" in that it must be compatible with the other ingredients of the formulation. It must also be suitable for use in contact with any tissues or organs with which it may come in contact, meaning that it must not carry a risk of toxicity, irritation, allergic response, immunogenicity, or any other complication that excessively outweighs its therapeutic benefits.

The pharmaceutical compositions according to the invention can also be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, terra alba, magnesium stearate or stearic acid, talc, pectin, acacia, agar or gelatin. The carrier may also include a sustained release material such as glyceryl monostearate or glyceryl distearate, alone or with a wax.

The pharmaceutical preparations are made following the conventional techniques of pharmacy involving milling, mixing, granulation, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

The pharmaceutical compositions according to the invention may be delivered in a therapeutically effective amount. The precise therapeutically effective amount is that amount of the composition that will yield the most effective results in terms of efficacy of treatment in a given subject. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, for instance, by monitoring a subject's response to administration of a compound and adjusting the dosage accordingly. For additional guidance, see Remington: The Science and Practice of Pharmacy (Gennaro ed. $22^{nd}$ edition, Williams & Wilkins PA, USA) (2012).

Typical dosages of a therapeutically effective dosage of SIRT3 or PACAP, or agonists of receptors to SIRT3 or PACAP can be in the ranges recommended by the manufacturer where known therapeutic compounds are used, and also as indicated to the skilled artisan by the in vitro responses or responses in animal models. Such dosages typically can be reduced by up to about one order of magnitude in concentration or amount without losing the relevant biological activity. Thus, the actual dosage will depend upon the judgment of the physician, the condition of the patient, and the effectiveness of the therapeutic method based, for example, on the in vitro responsiveness of the relevant primary cultured cells or histocultured tissue sample, such as biopsied malignant tumors, or the responses observed in the appropriate animal models, as previously described.

The present invention is also directed to a kit to diagnose, prognose, or treat Alzheimer's disease or a neurological disorder. The kit is useful for practicing the inventive method of diagnosing or prognosing the disorder by determining the presence of one or more biomarkers, including expression levels of PACAP and/or SIRT3. The kit is an assemblage of materials or components, including at least one of the inventive compositions.

The exact nature of the components configured in the inventive kit depends on its intended purpose. For example, some embodiments are configured for the purpose of treating Alzheimer's disease. In one embodiment, the kit is configured particularly for the purpose of treating mammalian subjects. In another embodiment, the kit is configured particularly for the purpose of treating human subjects. In further embodiments, the kit is configured for veterinary applications, treating subjects such as, but not limited to, farm animals, domestic animals, and laboratory animals.

Instructions for use may be included in the kit. "Instructions for use" typically include a tangible expression describing the technique to be employed in using the components of the kit to effect a desired outcome. Optionally, the kit also contains other useful components, such as, diluents, buffers, pharmaceutically acceptable carriers, syringes, catheters, applicators, pipetting or measuring tools, bandaging materials or other useful paraphernalia as will be readily recognized by those of skill in the art.

The materials or components assembled in the kit can be provided to the practitioner stored in any convenient and suitable ways that preserve their operability and utility. For example the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed by well known methods, preferably to provide a sterile, contaminant-free environment. As used herein, the term "package" refers to a suitable solid matrix or material such as glass, plastic, paper, foil, and the like, capable of holding the individual kit components. The packaging material generally has an external label which indicates the contents and/or purpose of the kit and/or its components.

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Among these variations, without limitation, are the selection of constituent modules for the inventive compositions, and the diseases and other clinical conditions that may be diagnosed, prognosed or treated therewith. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

Methods

Postmortem human brains were obtained from the Banner Sun Health Research Institute Brain and Body Donation Program (BBDP). The operations of the BBDP have been approved by the Western Institutional Review Board. Frozen brain tissues were obtained from patients with a clinical and pathological diagnosis of late onset AD and from age-matched cognitive normal subjects (CN). Brain donors all underwent extensive longitudinal clinical and neuropsychological assessment antemortem. All AD cases were selected as being "intermediate" or "high" probability for AD according to NIA-Reagan criteria (National Institute on Aging-Alzheimer's Association criteria). CN subjects did not meet the criteria for AD or dementia. The AD cases and controls did not differ significantly in their age at death, gender, or educational level. Cortical Aβ neuritic plaque density (CERAD evaluation) and Braak tangle stage were determined by a neuropathologist (T.G.B). Postmortem cisternal CSF samples from the same cohort were obtained.

Protein sample solution and CSF (AD=12 and CN=11) were quantified for PACAP expression using standard ELISA kit (Cat# MBS160511, MyBiosource Inc. San Diego, Calif.) according to the manufacture protocol. Briefly, samples were loaded and incubated with biotin-labeled PACAP antibody at 370 C for 60 minutes. The plated was washed with the washing buffer for five times, followed by incubation with chromogen solution at 370 C for 10 minutes. The reaction was stopped by adding stop solution. The final results were read at OB 450 nm. The ELISA result of PACAP levels in the brain were compared to the western blot result. The PACAP level measured was in the middle range of the standard curve and was correlated nicely with the western blot results (CN: Pearson's r=0.9093, P<0.01; AD: Pearson's r=0.8243, P<0.01).

Another set of postmortem brain samples (AD=34, CN=14) were used for transcriptome study. Briefly, brain sections were stained with a combination of Thioflavin-S (Sigma-Aldrich, Dallas, Tex.) and 1% neutral red (Fisher Scientific, Chicago, Ill.). Pyramidal neurons were identified and laser captured onto Arcturus CapSure Macro LCM Caps and extracted according to the manufacturer's protocol. Total RNA was isolated from the neuronal cell lysate with the Arcturus PicoPure RNA Isolation Kit with DNase I treatment using Qiagen's RNase-free DNase Set (Valencia, Calif.). Isolated total RNA from each sample of ~500 neurons was double-round amplified, cleaned, and biotin labeled with Affymetrix's GeneChip per the manufacturer's protocol. Amplified and labeled cRNA was quantitated on a spectrophotometer and run on a 1% Tris-acetate-EDTA (TAE) gel to check for an evenly distributed range of transcript sizes 8.

T-tests were used to compare values of two groups. For comparing values across multiple groups, a one way ANOVA with post-hoc Tukey's test was used. Pearson's correlation assay was applied for correlation analyses. All results were reported as mean+standard error. Statistical significance was set at $P<0.05$.

PACAP is Reduced in Multiple Areas of Human AD Brain.

Neurons were laser captured and micro-dissected from multiple brain regions of AD patients and CN subjects. ADCYAP1 (the PACAP gene) expression was significantly reduced in AD (Table 1.1). Overall, the inventors identified significantly decreased neuronal expression of ADCYAP1 in the Middle Temporal Gyrus (MTG), Superior Frontal Gyrus (SFG), and Primary Visual Cortex (PVC). To validate this neurotranscriptome-based screening, they selected a different cohort of 12 cases of AD postmortem brain samples and 11 CN cases. They used ELISA to quantify PACAP protein expression. The PACAP protein levels were reduced in AD in all three regions and entorhinal cortex (ENT) (Table 1.2).

TABLE 1.1

Neurotranscriptome of ADCYAP1 gene expression

| Gene | Brain region | Fold change | P value |
| --- | --- | --- | --- |
| ADCYAP1 | ENT | −3.702532581 | 0.127300685 |
| ADCYAP1 | MTG | −4.039581566 | 0.005626227 |
| ADCYAP1 | SFG | −8.911001119 | 0.008381943 |
| ADCYAP1 | PVC | −5.904469845 | 0.00228059 |

ADCYAP1 is the PACAP gene.
ENT = Entorhinal Cortex,
MTG = Middle Temporal Lobe
SFG = Superior Frontal Cortex,
PVC = Primary Visual Cortex

TABLE 1.2

ELISA quantification of PACAP

| | CN | | | AD | | |
|---|---|---|---|---|---|---|
| | PACAP (Mean ± SEM, ×$10^{-2}$ ng/mg protein) | N | | PACAP (Mean ± SEM, ×$10^{-2}$ ng/mg protein) | N | P value |
| ENT | 2.13 ± 0.25 | 11 | | 1.41 ± 0.19 | 12 | 0.035 |
| MTG | 1.24 ± 0.11 | 8 | | 0.73 ± 0.05 | 11 | 0.007 |
| SFG | 6.35 ± 0.33 | 8 | | 3.63 ± 0.22 | 10 | 0.001 |
| PVC | 5.98 ± 0.35 | 7 | | 3.86 ± 0.45 | 11 | 0.004 |

PACAP levels were normalized with total protein (mg) of the brain tissue. Data were presented as Mean + standard error.
ENT = Entorhinal Cortex,
MTG = Middle Temporal Lobe,
SFG = Superior Frontal Cortex,
PVC = Primary Visual Cortex,
AD = Alzheimer's disease,
CN = cognitively normal controls.

PACAP Reduction is Associated with Pathological Hallmarks of AD

Figure 1E:
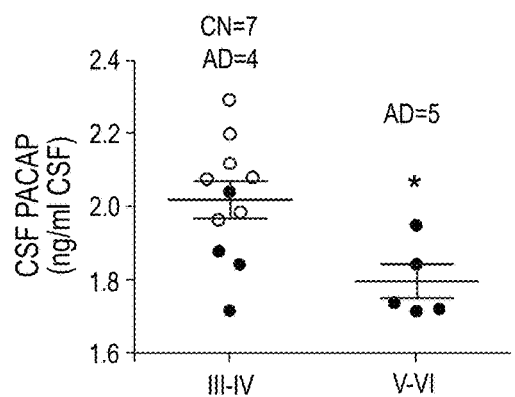

Amyloid plaques and neurofibrillary tangle are the two pathological hallmarks of AD. PACAP protein levels were inversely correlated with CERAD amyloid plaque score in the ENT and SFG but not in the MTG or PVC (FIGS. 1A-1D), suggesting that lower PACAP level is associated with a more pronounced Aβ deposition. In terms of neurofibrillary tangles, the AD cases had Braak stages ranging from IV to VI, whereas the CN samples ranged from III-IV. PACAP levels were reduced in Braak stage V-VI (all AD cases) than in stage III-IV (FIG. 1E). It's noteworthy that in the same Braak stage III-IV, AD cases had lower PACAP levels than CN cases; suggesting PACAP might be a more sensitive biomarker than tau pathology.

Pacap Levels in Csf Reflex its Levels in Brain

Figure 2A:
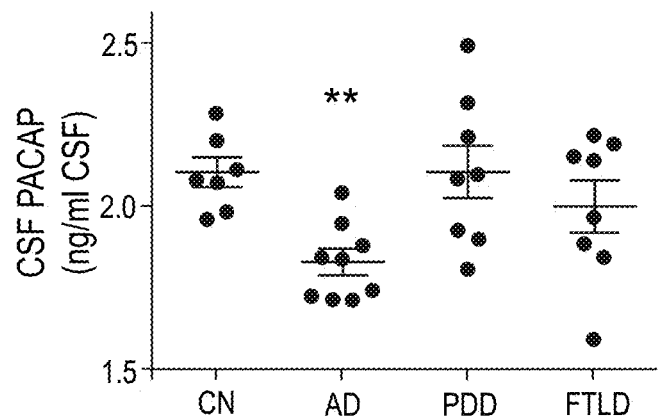
FIGS. 2A-2B depict, in accordance with embodiments herein, reduction in PACAP levels in CSF is specific to AD. PACAP levels were quantified by ELISA as ng PACAP per ml undiluted CSF.
Figure 2B:
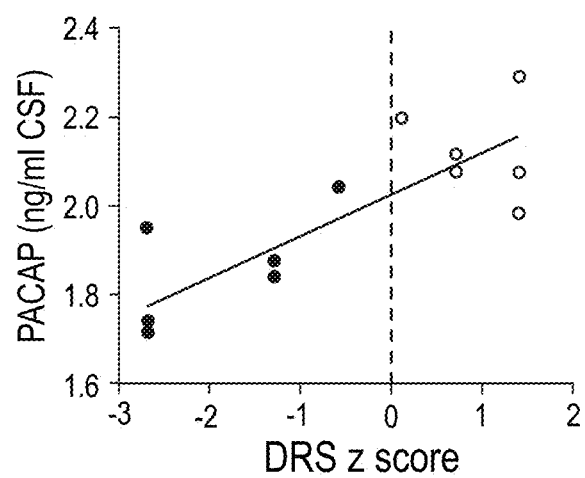

In AD cases, the PACAP level in CSF was reduced as compared with CN (1.83±0.11 ng/ml in AD, N=9, vs. 2.10±0.04 ng/ml in CN, N=7, p<0.01, FIG. 2A). In contrast, PACAP levels in Parkinson Disease with Dementia (PDD) (2.11±0.08 ng per ml CSF, N=8) and in Frontotemporal Lobe Dementia (FTLD) (2.01±0.07 ng per ml CSF, N=8) was comparable to that of CN (FIG. 2A). Furthermore, the PACAP level in CSF was strongly correlated with the Mattis Dementia Rating Scale-Revised (DRS-R), a measure of global cognitive functioning (Pearson's r=0.8197, p=0.0001, FIG. 2B herein).

Generally

In the four brain areas examined, both PACAP mRNA transcription and protein expression are significantly reduced in AD brains compared to matched CN controls. PACAP levels in the CSF were also significantly decreased in AD versus controls. This supports that the reduced neurotrophic effects from PACAP is an important factor contributing to Alzheimer's pathology.

The CERAD amyloid plaque burden is inversely correlated with PACAP expression in the ENT and SFG, but not the MTG or PVC. This is not surprising because amyloid deposition usually spares the PVC unless in the case of posterior cortical atrophy. This concurs with the animal study showing that PACAP may inhibit the amyloidogenic processing and facilitate amyloid clearance. The progression of neurofibrillary tangle is defined by Braak stage that follows the pathway from the entorhinal cortex to the temporal lobe and then to the distal neocortex. PACAP levels at stage III-IV (limbic) was relatively higher than those at the advanced stage V-VI (isocortical). Thus, PACAP is associated with both pathological hallmarks of AD.

PACAP as a neurotrophin is abundant in the brain. PACAP levels in the CSF can be a good surrogate for diagnosis and monitoring the disease progression since CSF is more readily available than brain biopsy. PACAP levels in the CSF are reduced in AD but not in PDD or FTLD, suggesting it is more specific to AD. This is consistent with the close relationship between PACAP and pathological markers of AD.

In summary, PACAP, an effective neurotrophin, is reduced in the pathonogmonic cortical regions of AD. PACAP levels inversely correlate with AD pathology. In addition to its role as an effective biomarker, therapeutic effects have been shown in animal models of AD.

Example 2

Methods

Postmortem human cerebral cortex and cerebrospinal fluid (CSF) were obtained from the Arizona Alzheimer's Disease Center and the Banner Sun Health Research Institute Brain and Body Donation Program (BBDP), including 16 AD, 9 MCI and 10 CN subjects. All AD cases were selected as being "intermediate" or "high" probability for AD according to NIA-Reagan criteria (National Institute on Aging-Alzheimer's Association criteria) (Consensus recommendations for the postmortem diagnosis of Alzheimer's disease. The National Institute on Aging, and Reagan Institute Working Group on Diagnostic Criteria for the Neuropathological Assessment of Alzheimer's Disease 1997). In addition, they were free of other neurodegenerative disorders such as vascular dementia, Parkinson's disease, dementia with Lewy bodies, frontotemporal dementia, hippocampal sclerosis, progressive supranuclear palsy, dementia lacking distinctive histology, multiple system atrophy, motor neuron disease with dementia and corticobasal degeneration. MCI was diagnosed by consensus as a syndrome of cognitive impairment beyond age-adjusted norms that is not severe enough to impair daily function or fulfill clinical criteria for dementia. To ensure MCI is an early stage of AD, we excluded 3 cases of MCI that didn't have AD pathology. All patients underwent longitudinal clinical and neuropsychological assessment antemortem. Since PACAP levels may change with age, only the final antemortem assessment score within one year prior to death, if available, was included for PACAP correlation analysis. The raw scores from Mattis Dementia Rating Scale (DRS), Stroop Color-Word Interference trial, the total words learned over trials (new learning) score, Auditory Verbal Learning Test total learning (AVLT-TL) and Judgment of Line Orientation (JLO) were converted to age- and education-corrected z scores.

We measured samples from parenchymal cortical homogenate including superior frontal gyms (SFG), middle temporal gyms (MTG), primary visual cortex (PVC), and from cerebrospinal fluid (CSF) samples. Protein samples and CSF were quantified for PACAP and PAC1 receptor using standard ELISA kit (Cat# MBS160511 and MBS042704, MyBiosource Inc. San Diego, Calif.) according to the manufacture protocol. Briefly, protein samples were loaded and incubated with biotin-labeled PACAP antibody or PAC1 receptor antibody at 37° C. for 60 minutes. The plate was washed with the washing buffer for five times, followed by incubation with chromogen solution at 37° C. for 10 minutes. The reaction was stopped by adding stop solution. The final results were read at OB 450 nm. In parallel, the protein quantity was determined with Pierce BCA protein assay kit (Cat#23227, Thermo Scientific, Rockford, Ill.). To eliminate the confounding factor of potential neurodegeneration, we normalized the PACAP level to the protein level in the brain tissue. Therefore, PACAP in cortical tissues was expressed as ng per mg total protein, whereas PACAP in CSF was expressed as ng/ml CSF.

We used ANOVA with post hoc Tukey pairwise comparisons and Pearson correlations, setting p<0.05 as the level of significance. All results are presented as mean±S.D in Table 2 and mean±S.E. in figures. We hypothesized the PACAP-PAC1 interaction would produce a net biological effect, which correlated with specific cognitive function. The ligand (L)-receptor (R) interaction pharmacodynamic model obeys the chemical kinetic principle. In this case, L represents PACAP and R represents PAC1 receptor. We assumed that the biological activity (cognitive performance in our case) is determined by the interaction of n mole of PACAP with each mole of PAC1 receptor. Therefore, $n[L]+[R]=[LnR]$->Biological activity. At equilibrium, $Kd=[LnR]/[L]^n[R]$, where Kd is the disassociation factor. Therefore, we hypothesized that the z score of cognitive performance is linearly proportional to $[L]^n[R]$. We did a series of linear correlation analyses between the product of $[PACAP]^n \times [PAC1]$ and cognitive performance z scores.

Results

Patient demographic data and final antemortem cognitive scores are summarized in the Table 2.

TABLE 2

Patient demographic and cognitive data

|  | Cognitive Normal (CN) | Mild Cognitive Impairment (MCI) | Alzheimer Disease (AD)[#] |
|---|---|---|---|
| Total case number | 10 | 9 | 16 |
| Gender (M/F) | 8/2 | 4/5 | 7/9 |
| Age, Mean (SD), years | 86.3 (5.7) | 87.2 (4.6) | 81.7 (8.9) |
| Most recent antemortem cognitive task performance[#] | | | |
| DRS z-score, Mean (SD) | 0.95 (0.50) | −0.85 (0.81)*** | −2.31 (0.65)*** |
| Stroop Words and Color Interference z score, Mean (SD) | 0.38 (1.05) | −0.83 (1.17) | −1.87 (1.11)*** |
| AVLT-TL z score, Mean (SD) | 0.34 (0.96) | −1.15 (0.89)* | −2.58 (1.73)*** |
| JLO z score, Mean (SD) | 1.33 (1.05) | 0.93 (0.84) | −1.03 (1.53)** |

Figure 3A:
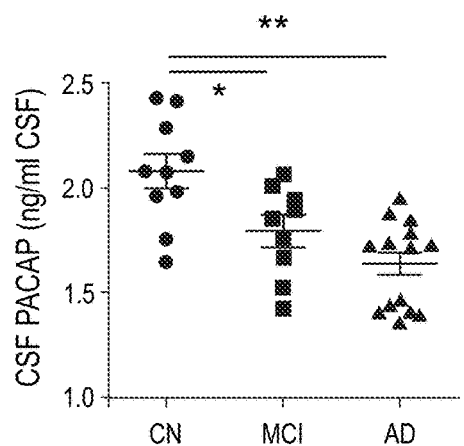
FIGS. 3A-3D depict, in accordance with embodiments herein, comparisons of PACAP abundance in selected cerebral regions among CN, MCI and AD.
Figure 3B:
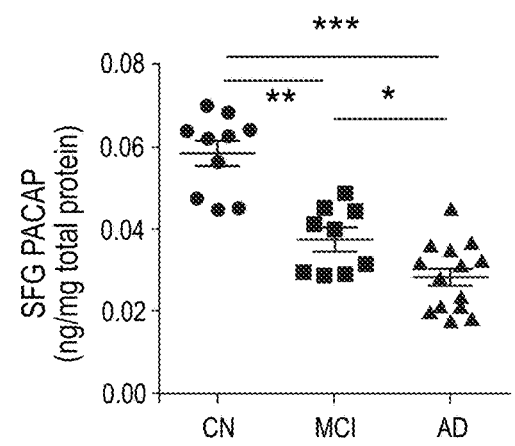
Figure 3C:
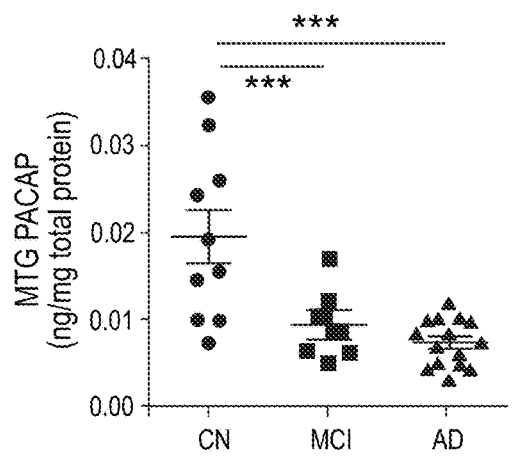
Figure 3D:
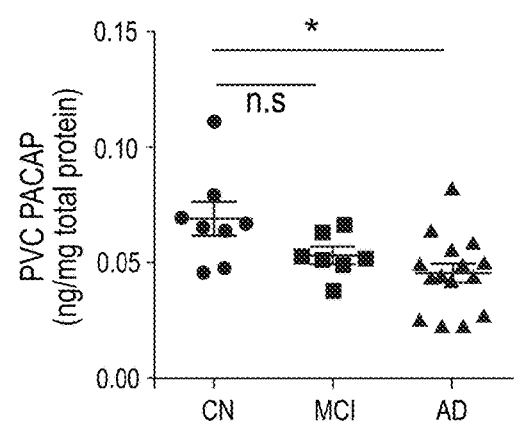

[#]Cognitive testing done within a year of death. DRS: Dementia Rating Scale-II, Stroop Color-Word Interference Trial, AVLT-TL: Auditory Verbal Learning Test total learning, JLO: Judgment of Line Orientation. All scores converted to z-scores based on age- and education-corrected norms.
*p < 0.05, P < 0.01, *p < 0.001, compared to CN, one way ANOVA with post hoc Tukey analysis The average age was similar among the three groups. PACAP levels in CSF were reduced in AD patients (1.61±0.06 ng/ml, n=16, p<0.01) compared to CN subjects (2.08±0.08 ng/ml, n=10). Noteworthy, PACAP in MCI patients (1.80±0.07 ng/ml, n=9, p<0.05) was also significantly reduced, albeit to a lesser extent (FIG. 3A). This progressive reduction of PACAP from CN to MCI and to AD was also apparent in SFG and MTG. PACAP in SFG (FIG. 3B) was reduced in MCI [$(3.77\pm0.26)\times10^{-2}$ ng/mg, n=9, p<0.01] and AD patients [$(2.85\pm0.19)\times10^{-2}$ ng/mg, n=16, p<0.001] compared to CN subjects [$(5.87\pm0.31)\times10^{-2}$ ng/mg, n=10]. PACAP in MTG (FIG. 3C) in MCI [$(0.95\pm0.16)\times10^{-2}$ ng/mg, n=8, p<0.001] and in AD patients [$(0.75\pm0.06)\times10^{-2}$ ng/mg, n=16, p<0.01] was reduced compared to that of CN subjects [$(1.95\pm0.31)\times10^{-2}$ ng/mg, n=10]. In PVC, PACAP (FIG. 3D) was reduced in AD patients [$(4.62\pm0.39)\times10^{-2}$ ng/mg, n=16, p<0.05] but not in MCI patients [$(5.31\pm0.36)\times10^{-2}$ ng/mg, n=7, p=0.18], compared to CN subjects [$(6.93\pm0.71)\times10^{-2}$ ng/mg, n=8]. Therefore, PACAP reduction is evident at MCI stage that precedes the onset of AD in the expected brain regions.

Figure 4A:
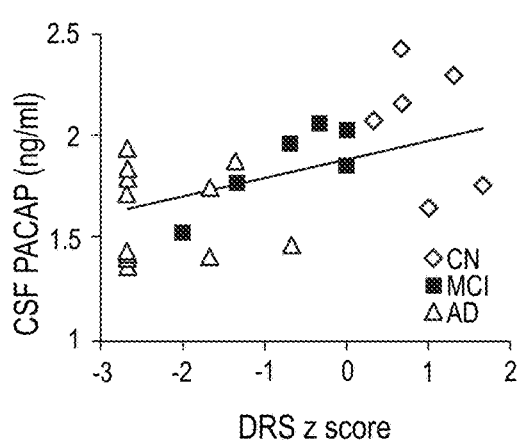
FIGS. 4A-4D depict, in accordance with embodiments herein, PACAP level in selected cerebral regions correlate with region-specific cognitive tests.
Figure 4B:
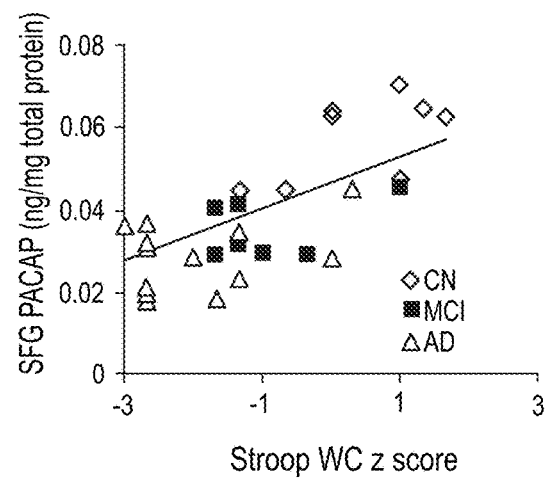
Figure 4C:
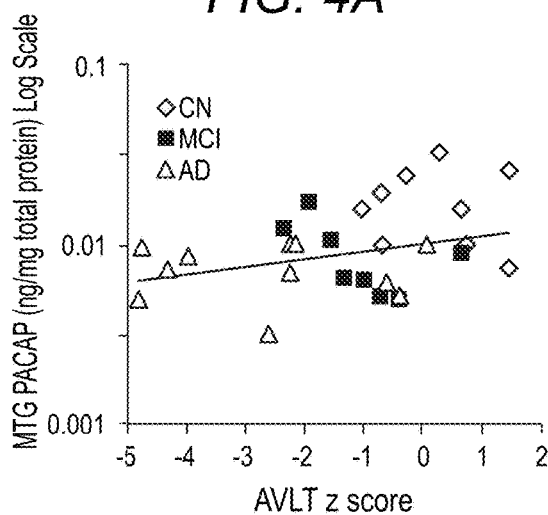
Figure 4D:
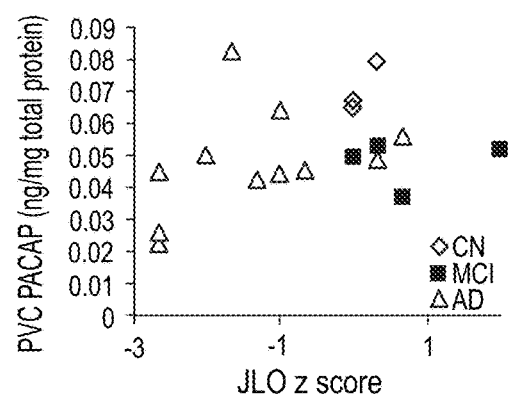
Figure 4E:
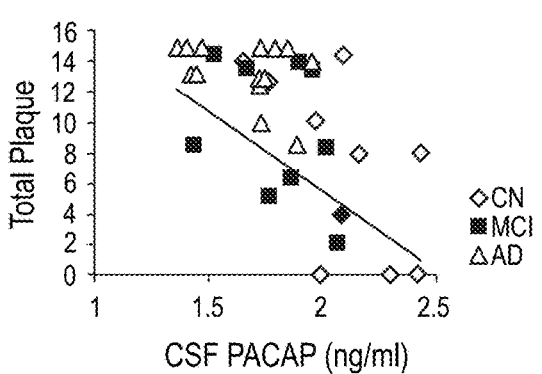
FIGS. 4E-4F depict, in accordance with embodiments herein, PACAP in CSF inversely correlate with total amyloid plaque and total tangles. Solid fitted lines indicate significant Pearson correlations ($p<0.05$).
Figure 4F:
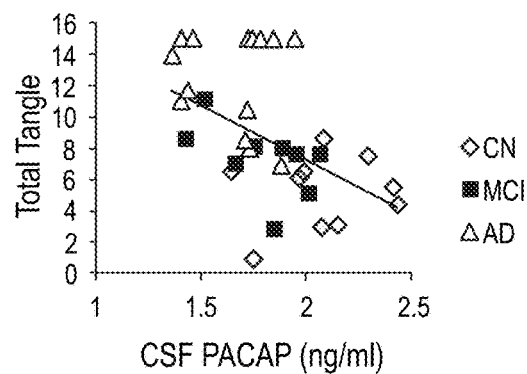

Since cognitive decline can occur in multiple cognitive domains, we analyzed the relationship between PACAP levels and cognitive performance. PACAP levels in CSF were correlated with DRS z-scores (Pearson r=0.503, p<0.05, FIG. 4A), suggesting the reduction of aggregated PACAP levels in CNS is correlated with poorer global cognitive function (DRS). Furthermore, PACAP levels in SFG were correlated with Stroop Color-Word Interference z-scores (Pearson r=0.584, p<0.01, FIG. 4B), a task that is sensitive to frontal lobe function. The PACAP levels in the MTG correlated with the AVLT-TL (Pearson r=0.329, p<0.05, FIG. 4C), a task that is sensitive to temporal lobe function. By contrast, PACAP levels in PVC did not correlate with JLO (p=0.14, FIG. 4D), a visuospatial task sensitive to occipitoparietal functioning. In addition, the CSF PACAP level inversely correlates with the total amyloid plaque number (r=−0.4805, p<0.01, FIG. 4E) and total tangles numbers (r=−0.5464, p=0.01, FIG. 4F).

Figure 5A:
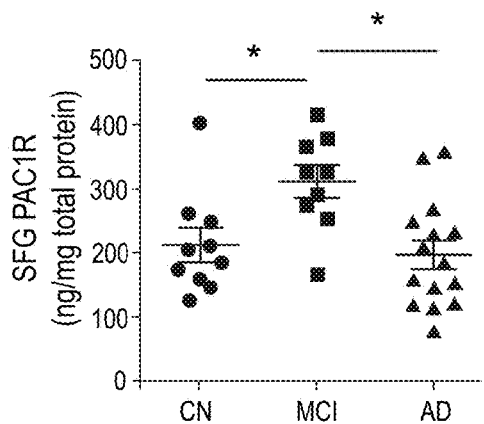
FIGS. 5A-5E depict, in accordance with embodiments herein, PAC1 receptor in selected cerebral regions and the PACAP-PAC1 receptor interaction.
Figure 5B:
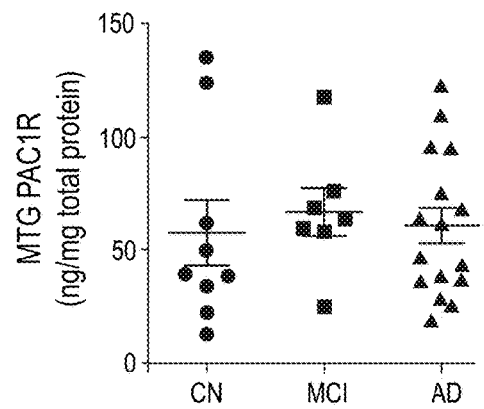
Figure 5C:
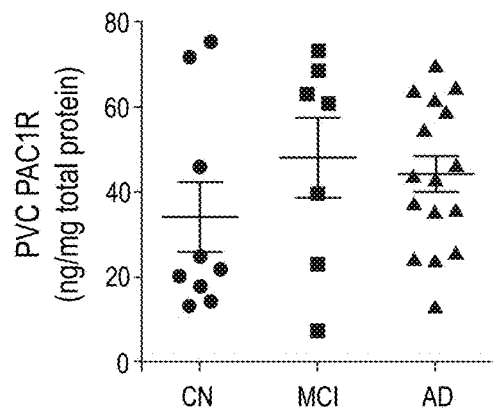

Since PACAP exert its physiological function by binding to PAC1 receptors in the brain, we measured the quantity of PAC1 receptors in SFG, MTG and PVC. As PAC1 receptors are located on the cell membrane, they are not detectable in CSF. In SFG, the PAC1 level in the AD group (199±22 ng/mg, n=16) was not different from that of controls (213±25 ng/mg, n=10, FIG. 5A). Interestingly, PAC1 level in MCI (312±25 ng/mg, n=9, p<0.05) was higher than that of controls (FIG. 5A). However, this PAC1 receptor upregulation in MCI was not observed in MTG or PVC. PAC1 in MTG was 58±14 in CN (n=9), 67±10.4 in MCI (n=8) and 61±7.9 in AD (n=16, p=0.47, FIG. 5B). PAC1 in PVC was 34±8.2 in CN (n=9), 48±9.5 in MCI (n=8) and 44±4.2 in AD (n=16, p=0.51, FIG. 5C). The relative abundance of PAC1 receptor was SFG>>MTG>PVC, and was not affected by the disease stages, i.e. MCI or AD.

Figure 5D:
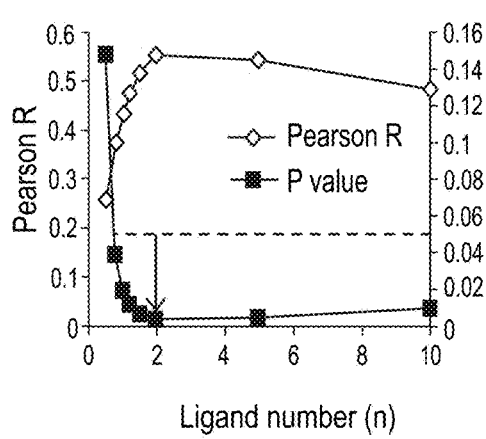
Figure 5E:
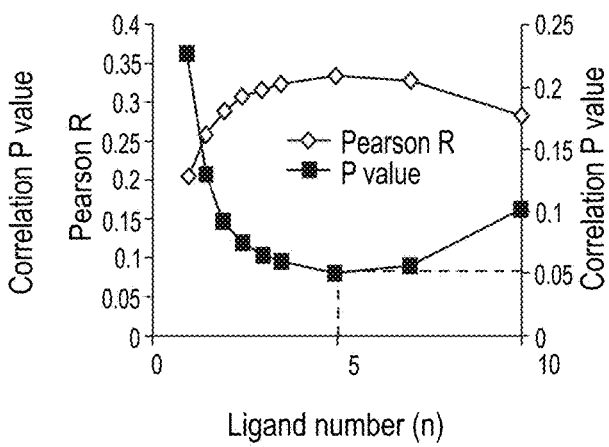

According to the pharmacodynamic model, the interaction of ligand and receptor determines the biological activity. We hypothesized that the product of $[PACAP]^n \times [PAC1R]$ would predict the cognitive function. Based on the algorithms described in detail in methods, a series of Pearons R and associated correlation P value are calculated by varying ligand numbers in the range of zero to ten. The relationship between Pearsons R (or P value) and ligand number (n) was fit into a polynomial relationship. In the SFG, 2 PCACP for each PAC1 receptor was required to reach a P value of less than 0.05 (FIG. 5D). This suggests a ratio of PACAP:PAC1 receptor at 2:1 best predicts the Stroop Word and Color interaction cognitive function in SFG. In MTG, more PACAP, at least 5, was required to bind to the PAC1 receptor to reach significant correlation with AVLT-TL. In PVC, P value nadir (P=0.16) did not reach significance regardless of the ligand number, suggesting the PACAP-PAC1 interaction in visual cortex did not predict JLO. Thus, the ligand-receptor interaction predicts regional cognitive function best in SFG, less so in MTG, and failed in PVC.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

What is claimed is:

1. A method of diagnosing late onset Alzheimer's disease (LOAD) in an individual, comprising:
   obtaining a cerebrospinal fluid sample from the individual;
   preparing the sample to be assayed by a serological test to determine the presence or absence of low PACAP expression levels;
   diagnosing LOAD based on the presence of low PACAP protein levels relative to those levels found in a healthy subject; and
   administering a composition comprising PACAP to the individual when the PACAP protein expression level in the individual's cerebrospinal fluid is below levels found in the healthy subject.

2. The method of claim 1, wherein the sample to be assayed by a serological test is prepared to determine the presence or absence of low PACAP protein expression, and LOAD is diagnosed based on the presence of low PACAP protein expression levels relative to those levels found in a healthy subject.

3. The method of claim 1 and further comprising assaying levels of SIRT3 protein levels in the sample from the individual.

4. The method of claim 3, wherein protein levels of at least of PACAP and SIRT3 in the cerebrospinal fluid sample are determined using an antibody-based assay.

5. The method of claim 4, wherein the antibody-based assay is selected from the following group: ELISA and flow cytometry.

6. The method of claim 1, wherein the composition comprises a pharmaceutically acceptable carrier.

7. A method of distinguishing between Alzheimer's disease and Parkinson's disease, comprising:
   obtaining a biological sample from a subject desiring a distinction between Alzheimer's disease and Parkinson's disease;
   assaying the biological sample to determine PACAP expression level;
   determining the subject has Alzheimer's disease if the PACAP expression level is lower than a reference value, or determining the subject does not have Alzheimer's disease if the PACAP expression level is not lower than the reference value; and
   administering a composition comprising PACAP to the subject if the subject is determined to have Alzheimer's disease.

8. The method of claim 7 and further comprising assaying the biological sample to determine SIRT3 expression level; and determining the subject has Alzheimer's disease if the PACAP expression level and the SIRT3 expression level are lower than their reference values, or determining the subject does not have Alzheimer's disease if the PACAP expression level and the SIRT3 expression level are not lower than their reference values.

9. The method of claim 7, wherein the composition comprises a pharmaceutically acceptable carrier.

10. The method of claim 7, wherein the biological sample comprises cerebrospinal fluid.

11. The method of claim 7, wherein the PACAP expression level comprises a PACAP protein expression level.

12. The method of claim 7, wherein assaying the PACAP expression level comprises measuring PACAP expression level using an antibody-based assay.

13. The method of claim 12, wherein the antibody-based assay is selected from the following group: ELISA and flow cytometry.

14. A method of detecting PACAP protein expression in a human subject suspected of having late onset Alzheimer's disease (LOAD), the method comprising the steps of:
   obtaining a cerebrospinal fluid sample from the human subject; and
   detecting an expression level of PACAP protein in the cerebrospinal fluid sample.

15. The method of claim 14 and further comprising detecting an expression level of SIRT3 protein in the cerebrospinal fluid sample.

16. The method of claim 14, wherein detecting the expression level of PACAP protein comprises measuring PACAP expression level using an antibody-based assay.

17. The method of claim 16, wherein the antibody-based assay is selected from the following group: ELISA and flow cytometry.

18. The method of claim 14 and further comprising:
   comparing the detected expression level of PACAP protein in the subject's sample to a reference level of PACAP protein; and
   administering a composition comprising PACAP to the subject if the subject's expression level of PACAP is below that of the reference level of PACAP protein.

* * * * *